United States Patent
Jiang et al.

(10) Patent No.: US 11,197,924 B2
(45) Date of Patent: Dec. 14, 2021

(54) PHOTOCHEMICAL PREPARATION METHOD FOR AUTOLOGOUS PLASMA INACTIVATED VACCINE FOR TREATING AIDS

(71) Applicant: Beijing Boxin Nature Biotech Ltd., Beijing (CN)

(72) Inventors: Miao Jiang, Beijing (CN); Hao Wu, Beijing (CN)

(73) Assignee: Beijing Boxin Nature Biotech Ltd., Beijing (CN)

( * ) Notice: Subject to any disclaimer, the term of this patent is extended or adjusted under 35 U.S.C. 154(b) by 0 days.

(21) Appl. No.: 16/844,763

(22) Filed: Apr. 9, 2020

(65) Prior Publication Data

US 2020/0237896 A1 Jul. 30, 2020

Related U.S. Application Data

(63) Continuation of application No. PCT/CN2019/081751, filed on Apr. 8, 2019.

(30) Foreign Application Priority Data

Apr. 23, 2018 (CN) .................. 201810368096.5

(51) Int. Cl.
| | | |
|---|---|---|
| A61K 48/00 | (2006.01) | |
| A61K 47/00 | (2006.01) | |
| A61K 9/127 | (2006.01) | |
| C07K 14/47 | (2006.01) | |
| C12N 15/85 | (2006.01) | |
| A61K 39/12 | (2006.01) | |
| A61P 31/18 | (2006.01) | |
| A61K 41/10 | (2020.01) | |
| A61L 2/00 | (2006.01) | |
| A61K 39/00 | (2006.01) | |

(52) U.S. Cl.
CPC .............. *A61K 39/12* (2013.01); *A61K 41/10* (2020.01); *A61L 2/0058* (2013.01); *A61P 31/18* (2018.01); *A61K 2039/5252* (2013.01)

(58) Field of Classification Search
CPC ............... A61K 38/00; A61K 38/1816; A61K 48/0066; A61K 9/1271; C07K 14/505
See application file for complete search history.

(56) References Cited

FOREIGN PATENT DOCUMENTS

| CN | 101190234 | * | 6/2008 |
|----|-----------|---|--------|
| CN | 101190234 A | | 6/2008 |
| CN | 102600521 | * | 7/2012 |
| CN | 102600521 A | | 7/2012 |
| CN | 108498795 A | | 9/2018 |

OTHER PUBLICATIONS

Ma, Y. et al., "Non-official translation: One Case of Therapy of HIV Infection by Means of Autologous Plasma Viral Inactivation Combined with Highly Active Antiretroviral Therapy", Medical Journal of Chinese People's Liberation Army), vol. 27, No. (9), Sep. 30, 2015, 114-116.

International Search Report and Written Opinion dated Jul. 26, 2019 in connection with International Application No. PCT/CN2019/081751.

International Preliminary Report on Patentability dated Nov. 5, 2020 in connection with International Application No. PCT/CN2019/081751.

* cited by examiner

*Primary Examiner* — Barry A Chestnut

(74) *Attorney, Agent, or Firm* — Wolf, Greenfield & Sacks, P.C.

(57) ABSTRACT

Disclosed herein is a photochemical preparation method of an autologous plasma inactivated vaccine for the treatment of acquired immune deficiency syndrome (AIDS), including the following steps: drawing autologous blood from an AIDS patient to form blood to be treated; separating the blood to obtain plasma to be treated; adding a photosensitizer into the plasma to be treated to form plasma to be inactivated; and subjecting the plasma to be inactivated to photochemical inactivation to obtain the autologous plasma inactivated vaccine.

12 Claims, 2 Drawing Sheets

PHOTOCHEMICAL PREPARATION METHOD FOR AUTOLOGOUS PLASMA INACTIVATED VACCINE FOR TREATING AIDS

RELATED APPLICATIONS

This application is a continuation of International Application No. PCT/CN2019/081751 filed Apr. 8, 2019, which claims priority to Chinese Application No. 201810368096.5 filed Apr. 23, 2018. The entire teachings of the above applications are incorporated herein by reference.

FIELD OF THE DISCLOSURE

The disclosure relates to the field of medicine, and in particular to, a photochemical preparation method of an autologous plasma inactivated vaccine for the treatment of acquired immune deficiency syndrome (AIDS).

BACKGROUND

AIDS is an extremely harmful infectious disease caused by AIDS virus (HIV virus) infection. HIV is a virus capable of attacking human body's immune system. It treats the most important CD4 T lymphocytes in the human immune system as the main target, destroying cells in large quantities and depriving the human body of immune function. Therefore, the human body is susceptible to various diseases, and may suffer from malignant tumors, resulting in high mortality rate.

Because the HIV virus is capable of damaging the human immune system and has extremely strong variability, it is difficult for existing drugs to eliminate the virus. Even if a drug can temporarily work, it will develop drug resistance over time and gradually weaken until it loses its therapeutic effect.

Therefore, how to make life expectancy of AIDS patients close to life expectancy of a normal person through treatment under the premise of effectiveness and safety is a technical problem to be urgently solved in the medical community.

SUMMARY

Embodiments of the disclosure provide a photochemical preparation method of an autologous plasma inactivated vaccine for the treatment of AIDS to solve the above problems.

The embodiments of the disclosure adopts the following technical solutions:

The embodiments of the disclosure provide a photochemical preparation method of an autologous plasma inactivated vaccine for the treatment of AIDS, comprising the following steps;

drawing autologous blood from an AIDS patient to form blood to be treated;

separating the blood to obtain plasma to be treated;

adding a photosensitizer into the plasma to be treated to form plasma to be inactivated;

subjecting the plasma to be inactivated to photochemical inactivation to obtain the autologous plasma inactivated vaccine.

Preferably, for the above photochemical preparation method of an autologous plasma inactivated vaccine for the treatment of AIDS, in the step of adding a photosensitizer into the plasma to be treated to form plasma to be inactivated:

adding the photosensitizer in the form of a mixed solution into the plasma to be treated.

Preferably, for the above photochemical preparation method of an autologous plasma inactivated vaccine for the treatment of AID, in the step of adding a photosensitizer into the plasma to be treated to form plasma to be inactivated:

the mixed solution being a mixed solution of physiological saline and the photosensitizer.

Preferably, for the above photochemical preparation method of an autologous plasma inactivated vaccine for the treatment of AIDS, in the step of adding a photosensitizer into the plasma to be treated to form plasma to be inactivated:

the photosensitizer being at least one of methylene blue, riboflavin, and psoralen.

Preferably, for the above photochemical preparation method of an autologous plasma inactivated vaccine for the treatment of AIDS, in the step of adding a photosensitizer into the plasma to be treated to form plasma to be inactivated:

the concentration of the photosensitizer in the mixed solution being 1 μmol/L to 1.3 μmol/L.

Preferably, for the above photochemical preparation method of an autologous plasma inactivated vaccine for the treatment of AIDS, in the step of adding a photosensitizer into the plasma to be treated to form plasma to be inactivated:

the concentration of the photosensitizer in the mixed solution being 1.2 μmol/L.

Preferably, for the above photochemical preparation method of an autologous plasma inactivated vaccine for the treatment of AIDS, in the step of adding a photosensitizer into the plasma to be treated to form plasma to be inactivated:

a volume ratio of the mixed solution to the plasma being 1:100.

Preferably, for the above photochemical preparation method of an autologous plasma inactivated vaccine for the treatment of AIDS, in the step of drawing autologous blood from an AIDS patient to form blood to be treated:

the amount of blood drawn being 600 to 1200 ml.

Preferably, for the above photochemical preparation method of an autologous plasma inactivated vaccine for the treatment of AIDS, in the step of drawing autologous blood from an AIDS patient to form blood to be treated:

the blood being drawn at least twice, and the amount of blood drawn each time being not more than 600 ml.

Preferably, for the above photochemical preparation method of an autologous plasma inactivated vaccine for the treatment of AIDS, in the step of drawing autologous blood from an AIDS patient to form blood to be treated:

for the AIDS patients with the body weight less than 60 kg, the amount of blood drawn each time being not more than 400 ml, and the total amount of blood drawn being not more than 800 ml;

for the AIDS patients with the body weight greater than 60 kg, the amount of blood drawn each time being not more than 600 ml, and the total amount of blood drawn being not more than 1200 ml.

Preferably, for the above photochemical preparation method of an autologous plasma inactivated vaccine for the treatment of AIDS, in the step of drawing autologous blood from an AIDS patient to form blood to be treated:

the AIDS patient being an AIDS patient without viral hepatitis disease.

Preferably, for the above photochemical preparation method of an autologous plasma inactivated vaccine for the treatment of AIDS, in the step of subjecting the plasma to be inactivated to photochemical inactivation to obtain an autologous plasma inactivated vaccine:

the wavelength of irradiating light being 610-650 nm, irradiation intensity being 40,000 to 80,000 lx, and irradiation time being 20 to 100 min.

Preferably, for the above photochemical preparation method of an autologous plasma inactivated vaccine for the treatment of AIDS, in the step of subjecting the plasma to be inactivated to photochemical inactivation to obtain an autologous plasma inactivated vaccine:

the wavelength of the irradiating light being 630 nm, the irradiation intensity being 50,000 to 60,000 lx, and the irradiation time being 30 min.

Preferably, for the above photochemical preparation method of an autologous plasma inactivated vaccine for the treatment of AIDS, in the step of subjecting the plasma to be inactivated to photochemical inactivation to obtain an autologous plasma inactivated vaccine used directly for autologous reinfusion:

the autologous plasma inactivated vaccine being not subjected to adsorption filtration.

The above at least one technical solution adopted by the embodiment of the disclosure can achieve the following beneficial effects:

The photochemical preparation method of an autologous plasma inactivated vaccine for the treatment of AIDS disclosed by the embodiments of the disclosure can prepare the autologous plasma inactivated vaccines, and human immunity can be effectively enhanced and HIV virus load is reduced after the vaccine is re-infused into the body of the AIDS patient itself.

DETAILED DESCRIPTION OF PREFERRED EMBODIMENTS

Figure 1:
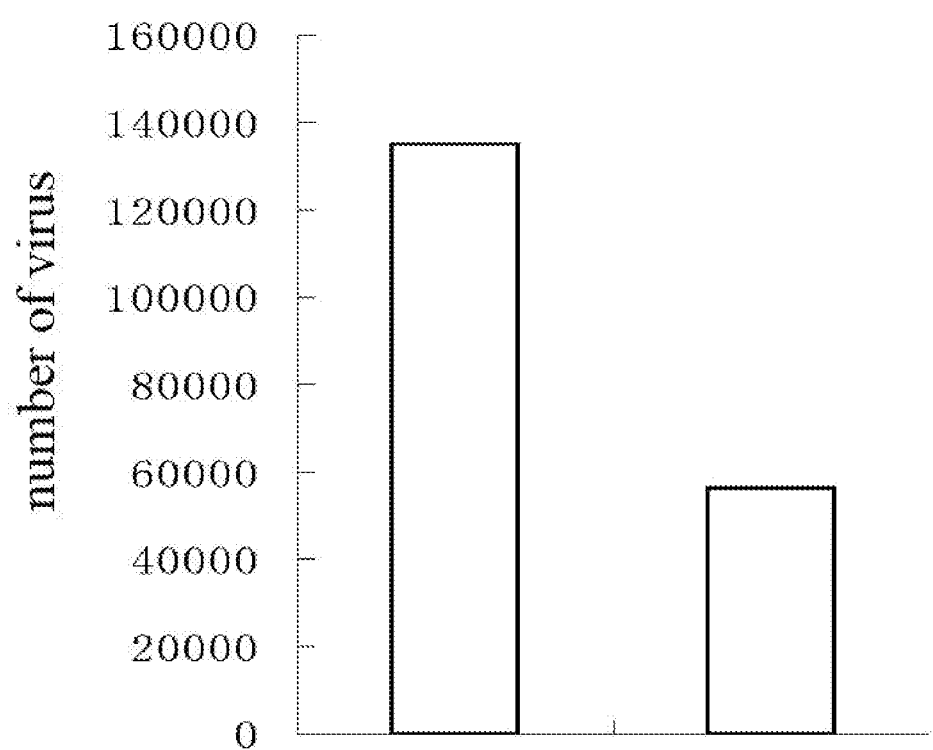
FIG. 1 is a view showing experimental results of inactivation effects of an autologous plasma inactivated vaccine provided by an embodiment of the disclosure on VSV virus.

In order to make the purposes, technical solutions and advantages of the disclosure clearer, the technical solutions of the disclosure will be clearly and completely described below in conjunction with the specific embodiments and the corresponding accompanying drawings. It is apparent that the described embodiments are merely part of the embodiments of the disclosure rather than all the embodiments. Based on the embodiments in the disclosure, all the other embodiments obtained by a person skilled in the art without paying creative work will fall into the protection scope of the disclosure.

The technical solutions provided by the embodiments of the disclosure are described in detail below.

An embodiment of the disclosure discloses a photochemical preparation method of an autologous plasma inactivated vaccine for the treatment of AIDS, and the method comprises the following steps:

S10. drawing autologous blood from an AIDS patient to form blood to be treated;

S20, separating the blood to obtain plasma to be treated;

S30, adding a photosensitizer into the plasma to be treated to form plasma to be inactivated;

S40: subjecting the plasma to be inactivated to photochemical inactivation to obtain the autologous plasma inactivated vaccine.

Because the HIV virus may damage the human immune system and has greatly strong variability, it is difficult for a single drug to serve to inhibit the virus. A vaccine is an autoimmune formulation for preventing infectious diseases prepared by artificially attenuating, inactivating or genetically modifying pathogenic microorganisms (such as bacteria, rickettsia, viruses, etc.) and their metabolites and other methods. The vaccine retains the characteristics of pathogenic bacteria capable of stimulating an immune system of an animal. When the animal contacts such harmless pathogenic bacteria, the immune system will produce a certain protective substances, such as immune hormones, active physiological substances, special antibodies, etc.; when the animal contacts the pathogenic bacteria again, the animal's immune system will follow its original memory and create more protective substances to prevent from the damage of the pathogenic bacteria.

Therefore, vaccines made from HIV viruses are highly targeted against and have greatly therapeutic effects on AIDS. However, due to the nature of the HIV virus itself, the HIV virus in every AIDS patient has its specific, which makes it difficult to obtain a universal vaccine to deal with every AIDS condition.

However, for each of the specific AIDS patients, attributes of HIV viruses in his/her body are relatively stable. Therefore, the HIV viruses carried by the AIDS patients themselves are treated and fabricated into the vaccine, which has extremely effective therapeutic effect on the AIDS patients themselves.

Because the HIV virus is abundantly present in the patient's blood or other body fluids and the content of the blood is the largest in these body fluids and the methods for obtaining the blood are also most mature, taking autologous blood from the AIDS patients is the most direct and safe way to obtain HIV virus. The first step in the preparation method of the disclosure is to draw autologous blood from an AIDS patient to form blood to be treated.

In order to obtain sufficient antigens, for a normal adult patient, 600-1200 ml of blood drawn is generally required during a single process for preparation of the vaccine. For minors or elderly people, adjustment may be made based on patient's physical conditions. Moreover, considering the patient's physical burden, blood is preferably drawn multiple times, and the amount of blood drawn each time is not more than 400 ml. There should be a certain time interval between two consecutive blood draws to allow the patient to get appropriate rest and recuperation.

Moreover, the total blood volume of different patients is certainly variable. If equal amounts of blood is taken from each patient, for a patient with large total blood volume, a ratio of the amount of blood drawn to the total blood volume of the patient itself is relatively low, and thus the therapeutic effect will be unsatisfactory, and for a patient with low total blood volume, the ratio of the amount of blood drawn to the total blood volume of the patient itself is relatively high, leading to the patient's physical discomfort or other symptoms due to ischemia. Therefore, it is necessary to appropriately adjust the amount of blood drawn based on the total blood volume of the patient.

For two ordinary patients, the patient with large body weight usually has more total blood volume. Although this phenomenon is not absolute and direct proportional linear relationship, it is still useful for determining the amount of blood drawn from the patients. Therefore, in the present embodiment, it is preferable to determine the amount of blood drawn based on the patient's body weight. Specifically, for the AIDS patients with the body weight less than 60 kg, the amount of blood drawn each time is not more than 400 ml, and the total amount of blood drawn is not more than 800 ml; for the AIDS patients with the body weight greater than 60 kg, the amount of blood drawn each time is not more than 600 ml, and the total amount of blood drawn is not more than 1200 ml. That is to say, larger amount of blood may be drawn each time from the AIDS patients with the body weight greater than 60 kg, and the total blood volume may also be larger.

A blood draw rate should be appropriate, and too slow blood draw rate may result in the death of the HIV virus inside the blood, reducing or losing the therapeutic effect of the vaccine. Too quick blood draw rate will impose a heavy burden on the human body, especially for AIDS patients with severe deficiency of immune system, and any negligence may be fatal. According to experimental tests, the blood draw rate ranging from 40 to 60 ml/min is a preferred range.

In addition, some AIDS patients are also patients suffering from viral hepatitis. In addition to HIV virus, they also carry hepatitis viruses, such as HBV virus and HCV virus. It can be experimentally found that the presence of these hepatitis viruses will have a negative impact on the therapeutic effect of the AIDS vaccine, and may even lead to the inability to detect the therapeutic effect of the vaccine. Therefore, in order to ensure the stable and detectable therapeutic effect of the vaccine and prevent from unknown risks, the vaccine of the disclosure preferably aims only at AIDS patients without viral hepatitis disease.

Blood is a red, opaque, and viscous liquid flowing through the blood vessels and heart of a person. The blood consists of plasma and blood cells. One liter of the plasma contains 900 to 910 grams of water, 65-85 grams of protein, and about 20 grams of low molecular species, such as various electrolytes and organic compounds, and the HIV virus is also present in the plasma. Therefore, the plasma may be separated from the blood cells by centrifugation or the like to obtain individual plasma to be treated.

The blood cells comprise three types of cells, including red blood cells, white blood cells and platelets. The blood cells have very important significance to the metabolism of human body, and basically have little effect on the preparation of the vaccine. Therefore, it is most preferable to quickly and simultaneously re-infuse these blood cells to the body of the patient after separation. Since the content of the platelet in the blood cell is extremely high and easy to coagulate, in order to maintain the fluidity of the blood cell, it is most preferable to add a certain amount of anticoagulants during the reinfusion process. In addition, it is also possible to simultaneously infuse physiological saline for the patient to supplement water, electrolytes and the like that are deficient in the blood.

The plasma to be treated obtained by the separation is guided to a collection bag through a catheter, and after sufficient amounts of the plasma was collected by the collection bag, the collection is stopped. The bag is sealed and transferred for the next operation. In order to facilitate the quick stop of the collection operation, the catheter may be sealed through hot-melt by a heat-sealing machine, which may simplify the sealing operation of the bag.

Next, the plasma to be treated obtained by the separation is subjected to inactivation, leading to the loss of its pathogenicity and forming an autologous plasma inactivated vaccine. Virus inactivation refers to a method in which a virus is killed by physical or chemical means, but a useful antigen in its body is not damaged. The physical inactivation method and the chemical inactivation method each may be subdivided into various ways. For example, the physical inactivation method may comprise ultrasonic inactivation, ultraviolet inactivation, radiation inactivation, high pressure inactivation, and the like. The chemical inactivation method may comprise photochemical inactivation, enzymatic chemical inactivation, and the like. Each inactivation method has its own suitable application range, and is unable to achieve the same effect on all viruses and bacteria. Therefore, it is very important to choose a method for inactivation. After extensive experiments, we found that photochemical inactivation is superior to other inactivation methods in inactivating HIV virus.

Before photochemical inactivation, the plasma to be treated obtained by the separation is firstly pretreated, which mainly comprises adding a photosensitizer into the plasma to be treated to form plasma to be inactivated. The photosensitizer is also known as a sensitizer, a sensitizing agent, and a photocrosslinker. In a photochemical reaction, the photosensitizer only absorbs photon, transfers energy to a molecule unable to absorb photon, and facilitates the molecule to undergo a chemical reaction, but it does not participate in the chemical reaction and returns to its original state. The photochemical reaction initiated by the photosensitizer is called a photosensitivity reaction. Generally, the photosensitivity reaction involving oxygen molecules and accompanied with biological effects is called a photodynamic reaction, and a drug that can initiate the photodynamic reaction to destroy a cell structure is called a photodynamic drug, that is, a photosensitive drug.

The purpose of adding the photosensitizer in the disclosure is to use it to promote the photochemical reaction, thereby inactivating the HIV virus. In order to impart better fluidity and dispersibility to the photosensitizer, it is preferable to add the photosensitizer into the plasma to be treated in the form of a mixed solution. The photosensitizer may be added into normal saline to form the mixed solution. The normal saline is a commonly used injection solution for daily injection, and has basically no side effect on the human body, and thus is very suitable to be used as a carrier for the photosensitizer. After formulating the mixed solution, it may be injected into the collection bag through a syringe.

There are many types of photosensitizers, and different types of photosensitizers have large differences in the photochemical inactivation effects on HIV virus. After experimental tests, the vaccines obtained with methylene blue, riboflavin or psoralen have the best therapeutic effect. Moreover, the photosensitizer may be used alone or in combination to enhance the inactivation effect.

The concentration of the photosensitizer is also an important indicator. If the amount of the photosensitizer is too low, the inactivation effect may be relatively poor, and the final therapeutic effect of the vaccine is also relatively poor. If the concentration of the photosensitizer is too high, on the one hand it may cause waste, and on the other hand the photosensitizer having a high concentration may also have a negative impact on the human body. It is experimentally determined that the concentration of the photosensitizer in the mixed solution is preferably from 1 μmol/L to 1.3

μmol/L, and preferably 1.2 μmol/L. When adding the plasma, a volume ratio of the mixed solution to the plasma is 1:100. After adding the photosensitizer into the plasma to be treated, it may also be shaken for a certain period of time to enable the photosensitizer to accelerate dispersion.

Finally, the collection bag containing the inactivated plasma is placed in a plasma virus inactivation device and subjected to the photochemical inactivation, finally obtaining an autologous plasma inactivated vaccine. The wavelength of irradiating light, irradiation intensity, and irradiation time during the inactivation process have an important influence on the inactivation effect, and therefore should be carefully selected. According to the experiments, the optimal wavelength of irradiating light ranges from 610 to 650 nm, and 630 nm is the most preferred wavelength value. The irradiation intensity should be maintained in the range of 40,000 to 80,000 lx, preferably in the range of 50,000 to 60,000 lx, and the irradiation time is 20 to 100 min, with an optimum value of 30 min.

Plasma inactivation with the photosensitizer has long been used in the field of traditional blood withdrawer (e.g., blood donation). Since the color of human plasma is usually yellow, the photosensitizer usually has a color characteristic different from blood and plasma, such as methylene blue exhibiting a noticeable blue color. After being inactivated, the plasma no longer presents its original color due to the residual photosensitizer. In order to protect the blood recipient from rejection, the plasma is usually subjected to adsorption filtration after inactivation, and its original color is thereby restored by removing the photosensitizer.

In the present embodiment, since the vaccine product is required, the killing effect of the autologous plasma inactivated vaccine on the virus is more desirable. We have experimentally found that the autologous plasma inactivated vaccine still has a strong inactivation effect on newly added viruses after subjecting to the photochemical inactivation.

Figure 2:
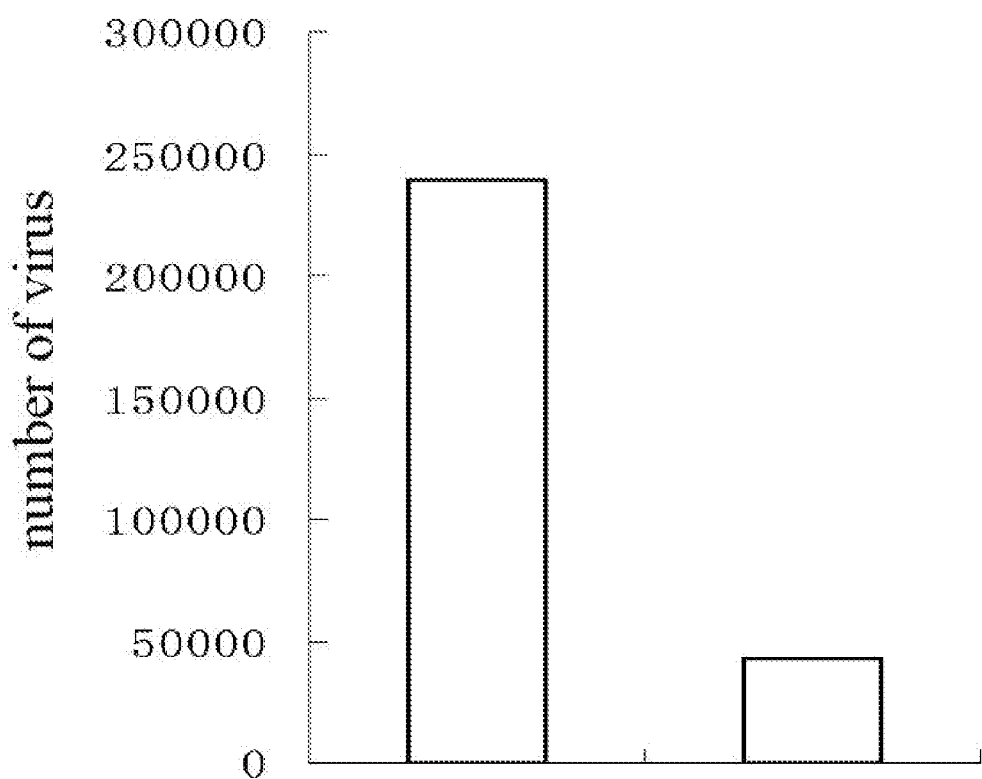
FIG. 2 is a view showing experimental results of inactivation effects of an autologous plasma inactivated vaccine provided by an embodiment of the disclosure on Sindbis virus.

Specifically with reference to FIG. 1 and FIG. 2, FIG. 1 shows the number of the viruses measured after adding equal amounts of VSV virus into the control group (left bar) and the autologous plasma inactivated vaccine (right bar), respectively. FIG. 2 shows the number of the viruses measured after adding equal amounts of Sindbis virus into the control group (left bar) and the autologous plasma inactivated vaccine (right bar), respectively. VSV virus, Sindbis virus and HIV virus are lipid-enveloped viruses. The experiment shows that the number of the viruses in the autologous plasma inactivated vaccine is significantly less than that of the control group, thereby demonstrating that the autologous plasma inactivated vaccine still has a relatively strong inactivation effect on newly added lipid-enveloped viruses.

It can be known from the principle of photochemical inactivation that the reason why caused the result is that there are still a large number of substances in the inactivated vaccine that are able to destroy the structure of the virus. This means that if the autologous plasma inactivated vaccine is directly re-infused into the AIDS patients, these substances will also have inactivating effect on the HIV virus in the patient's body, thereby improving the therapeutic effect.

Therefore, the autologous plasma inactivated vaccine in the present embodiment is directly formed by subjecting the plasma to be inactivated to photochemical inactivation and not to adsorption filtration during the process. A direct reinfusion mode without adsorption filtration during reinfusion is also employed in order to obtain a better therapeutic effect.

The obtained autologous plasma inactivated vaccine may be stored at room temperature for several hours. According to the therapeutic regimen, the autologous plasma inactivated vaccine is re-infused into the patient as soon as possible after completing light irradiation. The reinfusion process may be achieved by liquid infusion. Because there is no rejection or other adverse reactions between the autologous plasma inactivated vaccine obtained in this way and the patient, the reinfusion rate is very fast and the reinfusion of 600 ml of the autologous plasma inactivated vaccine may be usually completed within 10 minutes. The therapeutic effect of this autologous plasma inactivated vaccine is very ideal by experimental test.

The following is a clinical trial of the autologous plasma inactivated vaccines obtained using the preparation method of the disclosure.

Experimental Example

None of the AIDS patients in each of the experimental examples did not suffer from viral hepatitis disease and had developed drug resistance to the traditional drug combination therapy. The preparation method of the autologous plasma inactivated vaccine was as follows: separately drawing autologous blood from different AIDS patients to form blood to be treated, in which the weight and amount of blood drawn of the patients in each experimental example was shown in Table 1; separating the blood to obtain plasma to be treated; adding a mixed solution containing methylene blue and physiological saline into the plasma to be treated at a volume ratio of 1:100, with 1.2 μmol/L of the concentration of methylene blue in the mixed solution, forming plasma to be inactivated; subjecting the plasma to be inactivated to photochemical inactivation. The wavelength of irradiating light was 630 nm, the irradiation intensity was maintained in the range of 50,000 to 60,000 lx, and the irradiation time was 30 min. The autologous plasma inactivated vaccine was obtained.

TABLE 1

|  | experimental example 1 | experimental example 2 | experimental example 3 | experimental example 4 | experimental example 5 | experimental example 6 |
|---|---|---|---|---|---|---|
| weight of patient (kg) | 62.5 | 55 | 57.5 | 65 | 67.5 | 56 |
| amount of blood drawn (ml) | 1200 | 800 | 800 | 1200 | 1200 | 800 |

The autologous plasma inactivated vaccine obtained by the preparation was re-infused into the body of the patient by liquid infusion, and the reinfusion process took about 15 minutes.

Control Example

Two patients who had developed drug resistance were treated with the combination therapy of traditional 3TC+TDF+kaletra drugs to form comparative examples 1 and 2.

Long-term follow-up of the AIDS patients in the above experimental examples and comparative examples was carried out, and blood was periodically drawn to analyze blood components. Analysis results of blood components for each experimental example and control example can be seen from Table 2.

TABLE 2

| Test Item | No. | Preliminary Screening | 4 W | 12 W | 24 W |
|---|---|---|---|---|---|
| CD4 (number/μl) | experimental example 1 | 211.54 | 228.64 | 332.89 | 397.08 |
| | experimental example 2 | 173.25 | 547.49 | 646.3 | 942.72 |
| | experimental example 3 | 136.21 | 143.58 | 173.01 | 163.08 |
| | experimental example 4 | 201.76 | 603.91 | 344.55 | 396.36 |
| | experimental example 5 | 16.52 | 44.51 | 78 | 110.4 |
| | experimental example 6 | 469.54 | 498.85 | 621.49 | 593.98 |
| | comparative example 1 | 182.14 | 179.21 | 183.25 | 191.02 |
| | comparative example 2 | 211.45 | 209.27 | 218.59 | 199.94 |
| VL (copies/μl) | experimental example 1 | 3442 | 5924 | 81 | TND |
| | experimental example 2 | 173452 | 305 | TND | TND |
| | experimental example 3 | 14640 | 371 | 98 | <40 |
| | experimental example 4 | 757462 | 429 | 5656 | 55 |
| | experimental example 5 | 84386 | 865 | 988 | TND |
| | experimental example 6 | 296286 | 307 | <40 | TND |
| | comparative example 1 | 4146 | 4185 | 5451 | 6092 |
| | comparative example 2 | 213500 | 209806 | 234521 | 225642 |

The CD4 index is an important indicator of testing the therapeutic effect. It can be seen from Table 2 that after the autologous inactivated vaccine had been re-infused into the patients in the experimental examples 1-6, their CD4 indices begin to rise gradually over time, and the patients' immunity is greatly increased, and the treatment gains remarkable results. Due to differences in patients' physical conditions and disease conditions, the increasing amplitude of CD4 index of each patient was different. The patient with the lowest increasing proportion also gains a nearly 20% increasing amplitude, and the patient with the highest increasing proportion gains a nearly 700% increasing amplitude. It can be seen that the autologous vaccines have remarkable therapeutic effects on the AIDS patients. However, the CD4 indices of the control examples did not change significantly, and their changing amplitudes were maintained below 10%, and the therapeutic effect was limited.

At the same time, the VL index is also an important indicator of testing the therapeutic effect. It can be seen from Table 2 that after the autologous inactivated vaccine had been re-infused into the patients in the experimental examples 1-6, their VL indices dropped significantly, in which the results of 4 groups of experimental examples were below the testing limit. The VL indices of the control examples did not change significantly and remained at a high level.

The photochemical preparation method of the autologous plasma inactivated vaccine for the treatment of AIDS provided by the embodiments of the disclosure can prepare the autologous plasma inactivated vaccines, and human immunity can be effectively enhanced and HIV virus load is reduced after the vaccine is re-infused into the body of the AIDS patient itself.

The differences between the various embodiments are mainly described in the above embodiments of the disclosure. Different optimized features between the various embodiments may be combined to form a more preferable embodiment as long as they are not contradictory to each other, which are not described in detail herein considering the brevity and conciseness of the description.

The above description is only illustrative examples of the disclosure and is not intended to limit the disclosure. For a person skilled in the art, the disclosure may have various changes and variations. Any modification, equivalent replacement, and improvement made within the spirit and principle of the disclosure should fall in the scope of the claims of the disclosure.

What is claimed is:

1. A photochemical preparation method of an autologous plasma inactivated vaccine for the treatment of AIDS, comprising the following steps:
   drawing autologous blood from an AIDS patient to form blood to be treated, wherein the AIDS patient does not have viral hepatitis disease;

separating the blood to obtain plasma to be treated;
adding a photosensitizer into the plasma to be treated to form plasma to be inactivated; and
subjecting the plasma to be inactivated to photochemical inactivation to obtain the autologous plasma inactivated vaccine;
wherein the autologous plasma inactivated vaccine is not subjected to adsorption filtration.

2. The photochemical preparation method of an autologous plasma inactivated vaccine for the treatment of AIDS according to claim 1, wherein the photosensitizer is added in the form of a mixed solution into the plasma to be treated.

3. The photochemical preparation method of an autologous plasma inactivated vaccine for the treatment of AIDS according to claim 2, wherein
the mixed solution is a mixed solution of physiological saline and the photosensitizer.

4. The photochemical preparation method of an autologous plasma inactivated vaccine for the treatment of AIDS according to claim 1, wherein
the photosensitizer comprises methylene blue, riboflavin, and/or psoralen.

5. The photochemical preparation method of an autologous plasma inactivated vaccine for the treatment of AIDS according to claim 1, wherein
the concentration of the photosensitizer in the mixed solution is 1 μmol/L to 1.3 μmol/L.

6. The photochemical preparation method of an autologous plasma inactivated vaccine for the treatment of AIDS according to claim 1, wherein
the concentration of the photosensitizer in the mixed solution is 1.2 μmol/L.

7. The photochemical preparation method of an autologous plasma inactivated vaccine for the treatment of AIDS according to claim 2, wherein
the volume ratio of the mixed solution to the plasma to be treated is 1:100.

8. The photochemical preparation method of an autologous plasma inactivated vaccine for the treatment of AIDS according to claim 1, wherein
the amount of blood drawn is 600 to 1200 ml.

9. The photochemical preparation method of an autologous plasma inactivated vaccine for the treatment of AIDS according to claim 1, wherein
the blood is drawn at least twice, and the amount of blood drawn each time is not more than 600 ml.

10. The photochemical preparation method of an autologous plasma inactivated vaccine for the treatment of AIDS according to claim 9, wherein
for the AIDS patients with the body weight less than 60 kg, the total amount of blood drawn each time is not more than 400 ml, and the total amount of blood drawn is not more than 800 ml; and wherein
for the AIDS patients with the body weight greater than 60 kg, the total amount of blood drawn each time is not more than 600 ml, and the total amount of blood drawn is not more than 1200 ml.

11. The photochemical preparation method of an autologous plasma inactivated vaccine for the treatment of AIDS according to claim 1, wherein
the photochemical inactivation comprises irradiation, wherein the wavelength of irradiating light is 610-650 nm, irradiation intensity is 40,000 to 80,000 lx, and irradiation time is 20 to 100 min.

12. The photochemical preparation method of an autologous plasma inactivated vaccine for the treatment of AIDS according to claim 11, wherein
the wavelength of the irradiating light is 630 nm, the irradiation intensity is 50,000 to 60,000 lx, and the irradiation time is 30 min.

\* \* \* \* \*